(12) United States Patent　　(10) Patent No.: US 9,410,466 B2
Surnilla et al.　　(45) Date of Patent: Aug. 9, 2016

(54) EXHAUST HUMIDITY SENSOR

(71) Applicant: Ford Global Technologies, LLC, Dearborn, MI (US)

(72) Inventors: Gopichandra Surnilla, West Bloomfield, MI (US); Richard E. Soltis, Saline, MI (US); Jacobus Hendrik Visser, Farmington Hills, MI (US); Stephen B. Smith, Livonia, MI (US); Timothy Clark, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 465 days.

(21) Appl. No.: 13/706,194

(22) Filed: Dec. 5, 2012

(65) Prior Publication Data

US 2014/0156172 A1　Jun. 5, 2014

(51) Int. Cl.
　　*F01N 11/00*　(2006.01)
　　*F02D 41/14*　(2006.01)
　　*G01N 19/10*　(2006.01)

(52) U.S. Cl.
CPC ............ *F01N 11/00* (2013.01); *F02D 41/1454* (2013.01); *G01N 19/10* (2013.01); *F01N 2560/02* (2013.01); *F01N 2560/022* (2013.01); *F01N 2560/025* (2013.01); *F01N 2560/026* (2013.01); *F01N 2560/028* (2013.01); *F01N 2560/20* (2013.01); *F02D 2041/1472* (2013.01); *Y02T 10/47* (2013.01)

(58) Field of Classification Search
CPC ............ F02D 41/1454; F02D 41/2454; F02D 2041/1472; F01N 2560/02; F01N 2560/022; F01N 2560/025; F01N 2560/026; F01N 2560/028; F01N 2560/20; F01N 11/00; F01N 11/002
USPC .................... 123/672, 676, 685; 60/289, 303; 701/109, 103–10, 102–105
See application file for complete search history.

(56) References Cited

U.S. PATENT DOCUMENTS

| 4,168,683 A | 9/1979 | Hata et al. |
| 4,993,386 A * | 2/1991 | Ozasa et al. .................. 123/25 J |
| 5,655,365 A * | 8/1997 | Worth et al. .................... 60/285 |

(Continued)

FOREIGN PATENT DOCUMENTS

| JP | S6287629 A | * | 4/1987 |
| JP | 62189333 A | * | 8/1987 |
| WO | 2011138387 A1 | | 11/2011 |

OTHER PUBLICATIONS

Anonymous, "Humidifier concept for cost effective humidification of air delivery in FC stack," IPCOM No. 000223254, Published Nov. 14, 2012, 20 pages.

(Continued)

*Primary Examiner* — Hung Q Nguyen
*Assistant Examiner* — Robert Werner
(74) *Attorney, Agent, or Firm* — Julia Voutyras; Alleman Hall McCoy Russell & Tuttle LLP

(57) ABSTRACT

Embodiments for adjusting engine operating parameters based on output from an exhaust humidity sensor are provided. One example method for an engine comprises based on a dew point of exhaust gas, adjusting an exhaust gas sensor heater configured to heat an exhaust gas sensor disposed in an exhaust passage of the engine, the dew point based on output from a humidity sensor disposed in the exhaust passage.

26 Claims, 7 Drawing Sheets

(56) References Cited

U.S. PATENT DOCUMENTS

| | | | |
|---|---|---|---|
| 6,450,018 B1 * | 9/2002 | Mobius | 73/114.75 |
| 7,715,976 B1 | 5/2010 | Xiao et al. | |
| 8,046,986 B2 * | 11/2011 | Chillar et al. | 60/39.52 |
| 8,141,356 B2 | 3/2012 | Leone et al. | |
| 8,370,017 B2 | 2/2013 | Weber et al. | |
| 8,479,494 B2 * | 7/2013 | Enomoto et al. | 60/276 |
| 2010/0236532 A1 | 9/2010 | Xiao et al. | |
| 2011/0132340 A1 | 6/2011 | Soltis | |

OTHER PUBLICATIONS

Anonymous, "Improved method for water injection for fuel cells," IPCOM No. 000226207, Published Mar. 21, 2013, 2 pages.

* cited by examiner

EXHAUST HUMIDITY SENSOR

FIELD

The present disclosure relates to an internal combustion engine.

BACKGROUND AND SUMMARY

Exhaust gas sensors may be used to control a variety of engine operating parameters. For example, U.S. Patent Application No. 2011/0132340 describes detection of exhaust gas water content using an exhaust gas sensor (e.g., a UEGO sensor), which is also used to control engine air-fuel ratio. However, during the duration in which the UEGO sensor is used to detect the exhaust water content, the sensor does not measure the exhaust air/fuel ratio. Therefore, during the water content detection period, the air/fuel controllability is lost.

The inventors herein have recognized the issues with utilizing an exhaust gas sensor to detect exhaust gas water content. Accordingly, embodiments for providing a dedicated exhaust gas water content sensor in an engine exhaust are provided. In one embodiment, a method for an engine comprises, based on a dew point of exhaust gas, adjusting an exhaust gas sensor heater configured to heat an exhaust gas sensor disposed in an exhaust passage of the engine, the dew point based on output from a humidity sensor disposed in the exhaust passage.

In this way, a humidity sensor in the exhaust passage of the engine may be used to determine the water content of the exhaust (and hence the dew point), rather than other exhaust gas sensors. By determining the dew point of the exhaust gas, the timing of activating the exhaust gas sensor heater may be adjusted to avoid rapid evaporation of condensate that has settled on the sensor when the dew point is greater than the temperature of the sensor, without compromising engine air-fuel ratio control. In some examples, the humidity sensor may also be utilized to determine the composition of the fuel used during combustion (e.g., ethanol and/or water content of the fuel) and the light-off temperature of a catalyst positioned in the engine exhaust. In doing so, accurate air-fuel ratio may be maintained even as fuel composition changes, and exhaust emissions may be controlled.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
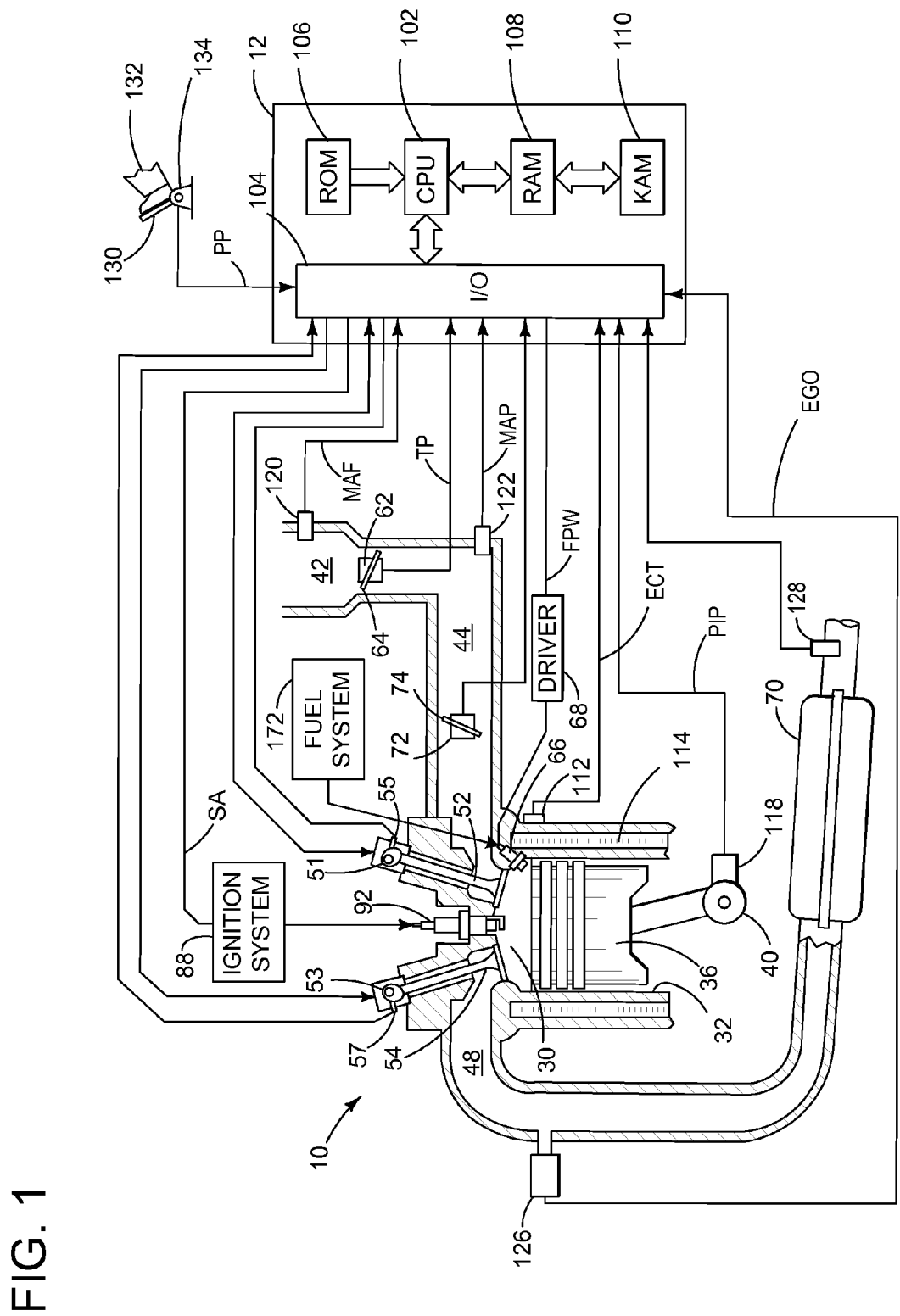
FIG. 1 shows a schematic diagram of an engine.
Figure 6:
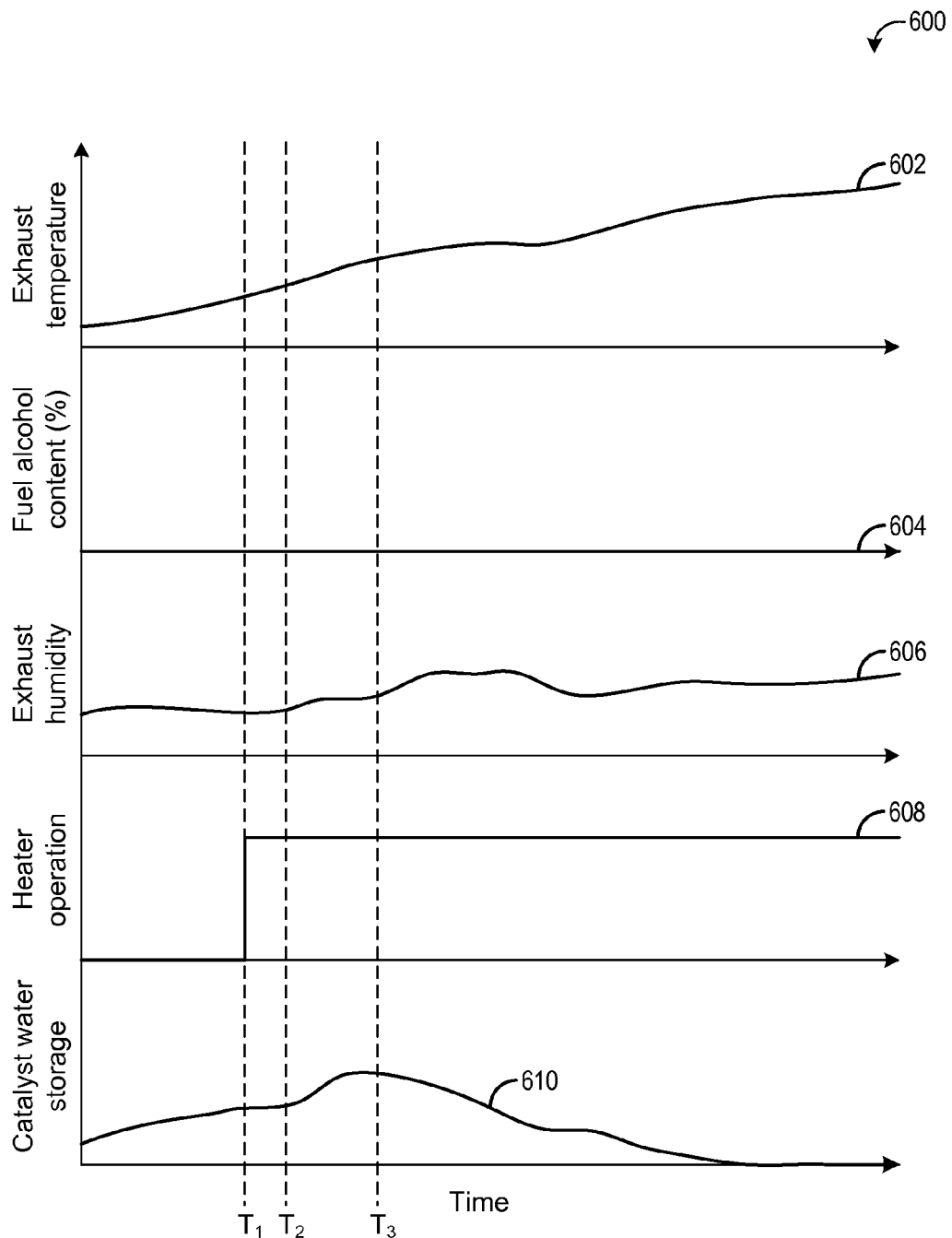
FIG. 6 is a diagram illustrating engine operating parameters during an engine cold start according to an embodiment of the present disclosure.
Figure 7:
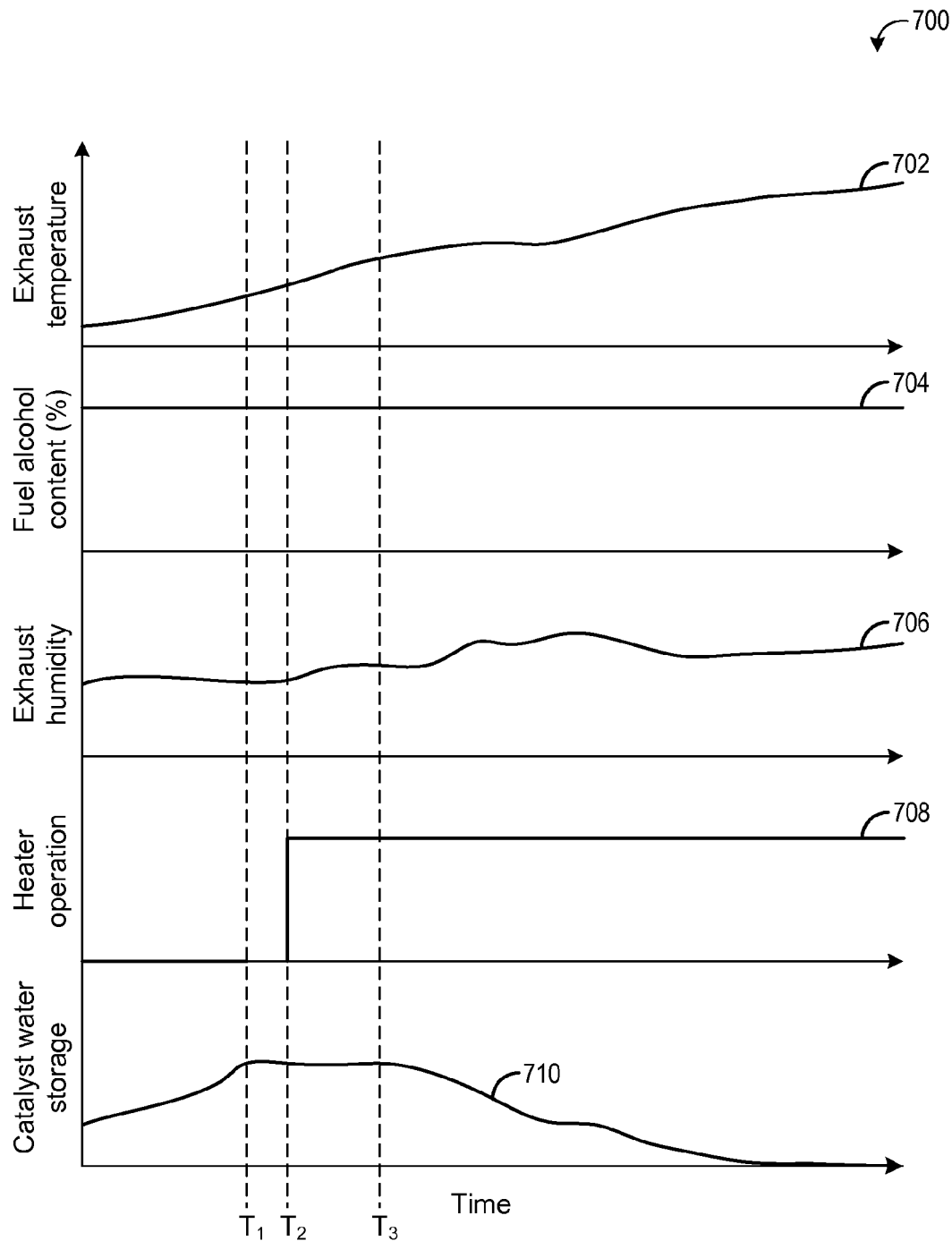
FIG. 7 is a diagram illustrating engine operating parameters during an engine cold start according to another embodiment of the present disclosure.

An exhaust humidity sensor may be used to determine or adjust a variety of engine operating parameters. For example, the humidity sensor output may indicate the alcohol or water content of the combusted fuel, and engine fueling amounts during a cold start may be adjusted based on the determined alcohol content. In another example, the humidity sensor may be used to determine when to activate an exhaust gas sensor heater to prevent cracking of the sensor resulting from rapid evaporation of condensate on the heater. The output of the humidity sensor may be affected by changes in the exhaust gas water content due to a catalyst disposed upstream of the humidity sensor. To compensate for these changes, the output of the humidity sensor may be corrected based on estimated stored or released water from the catalyst. These estimated catalyst water amounts may also be used along with output of the humidity sensor to determine the light-off temperature of the catalyst. FIG. 1 is an engine including a humidity sensor downstream of a catalyst and an engine controller, which may be used to carry out the methods illustrated in FIGS. 2-5. FIGS. 6 and 7 illustrate various operating engine parameters during execution of the above methods.

Referring specifically to FIG. 1, it includes a schematic diagram showing one cylinder of multi-cylinder internal combustion engine 10. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP.

Combustion cylinder 30 of engine 10 may include combustion cylinder walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion cylinder 30 may receive intake air from intake manifold 44 via intake passage 42 and may exhaust combustion gases via exhaust passage 48. Intake manifold 44 and exhaust passage 48 can selectively communicate with combustion cylinder 30 via respective intake valve 52 and exhaust valve 54. In some embodiments, combustion cylinder 30 may include two or more intake valves and/or two or more exhaust valves.

In this example, intake valve 52 and exhaust valve 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT) and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

Fuel injector 66 is shown coupled directly to combustion cylinder 30 for injecting fuel directly therein in proportion to the pulse width of signal FPW received from controller 12 via electronic driver 68. In this manner, fuel injector 66 provides what is known as direct injection of fuel into combustion cylinder 30. The fuel injector may be mounted on the side of the combustion cylinder or in the top of the combustion cylinder, for example. Fuel may be delivered to fuel injector 66 by a fuel delivery system (not shown) including a fuel tank, a fuel pump, and a fuel rail. In some embodiments, combustion cylinder 30 may alternatively or additionally include a fuel injector arranged in intake passage 42 in a configuration that provides what is known as port injection of fuel into the intake port upstream of combustion cylinder 30.

Fuel tank in fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios therebetween, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day to day variations in tank refilling can thus result in frequently varying fuel composition of the fuel in fuel system 172, thereby affecting the fuel composition and/or fuel quality delivered by injector 66. The different fuel compositions injected by injector 66 may hereon be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased.

Intake passage 42 may include a charge motion control valve (CMCV) 74 and a CMCV plate 72 and may also include a throttle 62 having a throttle plate 64. In this particular example, the position of throttle plate 64 may be varied by controller 12 via a signal provided to an electric motor or actuator included with throttle 62, a configuration that may be referred to as electronic throttle control (ETC). In this manner, throttle 62 may be operated to vary the intake air provided to combustion cylinder 30 among other engine combustion cylinders. Intake passage 42 may include a mass air flow sensor 120 and a manifold air pressure sensor 122 for providing respective signals MAF and MAP to controller 12.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 48 upstream of catalytic converter 70 (also referred to simply as catalyst 70). Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. Exhaust gas sensor 126 may include a heater that is configured to be activated when exhaust gas temperature is low, in order to heat the exhaust gas sensor 126 to its operating temperature. The exhaust system may include light-off catalysts and underbody catalysts, as well as exhaust manifold, upstream and/or downstream air-fuel ratio sensors. Catalytic converter 70 can include multiple catalyst bricks, in one example. In another example, multiple emission control devices, each with multiple bricks, can be used. Catalytic converter 70 can be a three-way type catalyst in one example.

A humidity sensor 128 may be disposed in exhaust passage 48. As depicted in FIG. 1, humidity sensor 128 may be disposed downstream of catalyst 70. However, other locations are possible, such as upstream of catalyst 70. Humidity sensor 128 may measure the relative humidity and temperature of the exhaust gas in exhaust passage 48. Based on the relative humidity and temperature, the specific humidity of the exhaust gas may be determined (e.g., the amount of water per unit mass of exhaust flow). Output from humidity sensor 128 may be sent to controller 12.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. The controller 12 may receive various signals and information from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Storage medium read-only memory 106 can be programmed with computer readable data representing instructions executable by processor 102 for performing the methods described below as well as variations thereof.

Storage medium read-only memory 106 can be programmed with computer readable data representing instructions executable by processor 102 for performing the methods described below as well as other variants that are anticipated but not specifically listed.

As described above, FIG. 1 shows only one cylinder of a multi-cylinder engine, and that each cylinder may similarly include its own set of intake/exhaust valves, fuel injector, spark plug, etc.

Figure 2:
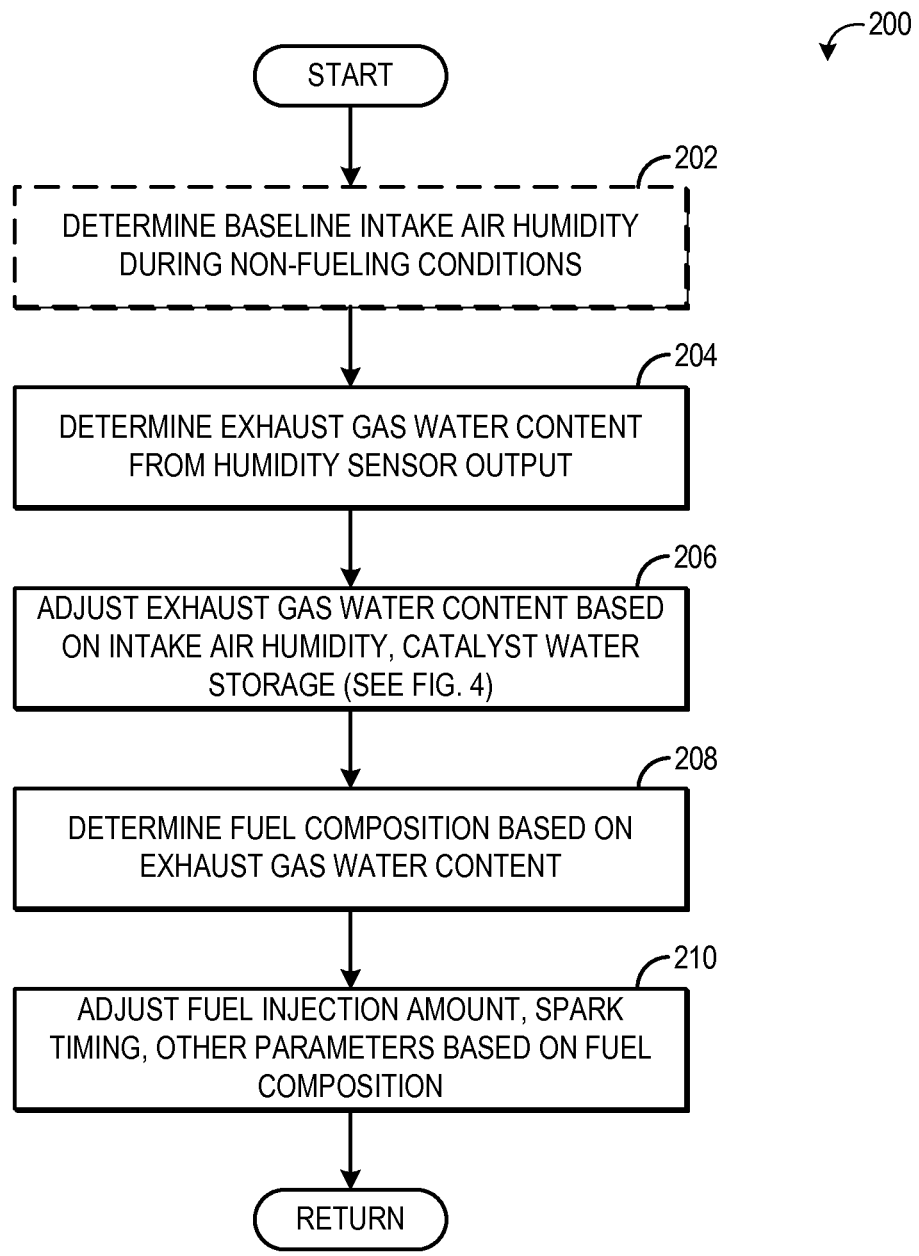
FIG. 2 is a flow chart illustrating a method for determining exhaust gas water content according to an embodiment of the present disclosure.

Turning to FIG. 2, a method 200 for determining fuel composition using a humidity sensor positioned in an engine exhaust is illustrated. Method 200 may be carried out by an engine controller (such as controller 12) according to instructions stored thereon, in order to determine fuel alcohol content using a humidity sensor (e.g., sensor 128). Method 200 may be performed every time the engine is operated, or it may be performed only when it is indicated that fuel composition be determined. For example, method 200 may be carried out in response to a fuel tank refill event. Method 200 optionally includes, at 202, determining a baseline intake air humidity during non-fueling conditions. The humidity sensor may output the relative humidity of the exhaust gas, which may be used with the exhaust gas temperature to determine the specific humidity of the exhaust gas (e.g., exhaust gas water content). The amount of water in the exhaust gas reflects not only the amount of alcohol and water in the fuel that is combusted in the engine, but also the amount of water present in the intake air. To determine the amount of water in the intake air, the humidity sensor output may be collected during a non-fueling condition. The non-fueling condition may include deceleration fuel shut-off, where the engine temporarily operates without receiving fuel during a deceleration event, prior to commencement of fuel injection during an engine start, or other suitable condition. However, instead of using the exhaust humidity sensor to determine intake humidity during non-fueling conditions, a humidity sensor may be present in the intake to determine the humidity of the intake air during fueling conditions.

At 204, the exhaust gas water content is determined from the exhaust humidity sensor output. As explained above, the exhaust humidity sensor output may be used to determine the water content of the exhaust gas. The water content indicates the amount of water per unit mass of the exhaust gas, and thus, the mass air flow through the engine and exhaust system is also determined to calculate the exhaust gas water content. At 206, the exhaust gas water content may be adjusted based on intake air humidity, catalyst water storage, and/or other additional parameters that may affect the exhaust gas water content determination. The exhaust gas water content determined by the humidity sensor may be corrected to remove the water content in the exhaust originating from the intake air. In this way, the adjusted exhaust gas water content may only reflect the amount of water resulting from the combusted fuel. Further, if the humidity sensor is positioned downstream of an exhaust catalyst or other aftertreatment device, the amount of water stored in the catalyst or released from the catalyst during the exhaust gas water content determination may be estimated to compensate the humidity sensor reading for water stored or released by the catalyst. For example, if the catalyst is storing water, the output from the humidity sensor may indicate a lower exhaust gas water content than is actually being produced by the engine. Additional information regarding determining the amount of stored or released water in the catalyst will be explained below with respect to FIG. 4.

At 208, the fuel composition is determined based on the exhaust gas water content. Fuel alcohol content may be mapped to exhaust gas water content. For example, an exhaust gas water content of around 83 g/Kg may indicate the engine is combusting gasoline, while an exhaust gas water content of around 111 g/Kg may indicate the engine is combusting a fuel blend of 85% ethanol and 15% gasoline. The controller may access a look-up table to determine the fuel alcohol content. The fuel alcohol content determined from the look-up table may be modified based on air-fuel ratio or other parameters, in order to account for incomplete combustion or other variables. Further, the amount of water in the fuel may be determined under some conditions. For example, if the engine is operating with 100% ethanol fuel, the amount of water in the fuel may vary, and thus the humidity sensor may be used to determine the water content of the fuel.

At 210, engine operating parameters may be adjusted based on the determined fuel composition. Adjusted engine operating parameters may include a fuel injection amount, spark timing, or other parameters. In one example, the amount of fuel injected to the engine during a cold engine start may be adjusted based on the determined fuel alcohol content, in order to prevent under or over-fueling that may lead to engine start issues or excessive emissions. In one example, the fuel injection amount may be increased if the exhaust gas water content is greater than a threshold, and decreased if the exhaust gas water content is less than the threshold. The threshold may be an expected amount of exhaust gas water content (for example, an expected amount of water produced by combusting a default fuel, such as gasoline). The engine operating parameters may be adjusted immediately upon determining the fuel composition. However, the fuel composition may be stored in the memory of the controller, and the operating parameters may be adjusted during subsequent engine operation.

Figure 3:
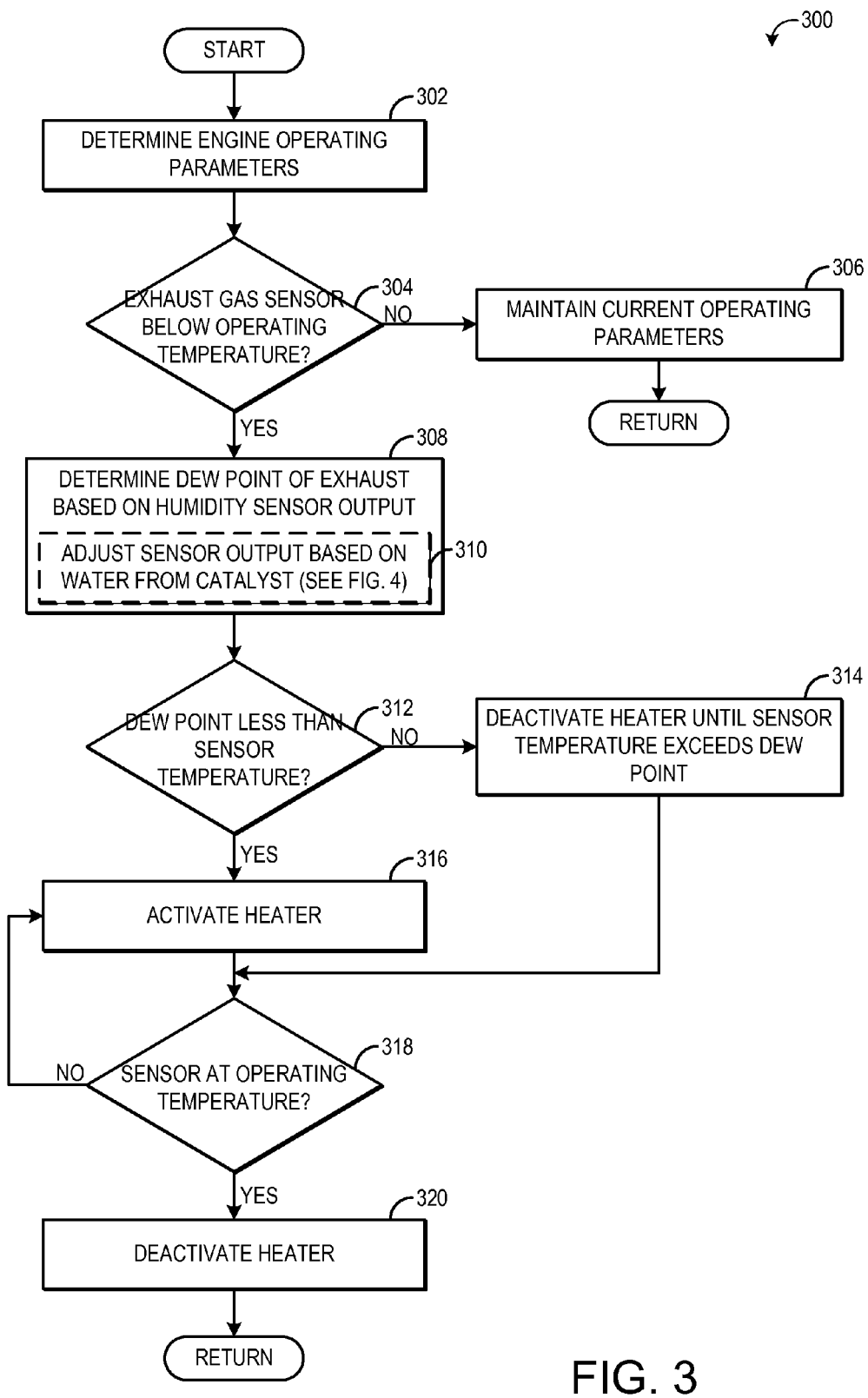
FIG. 3 is a flow chart illustrating a method for controlling an exhaust gas sensor heater according to an embodiment of the present disclosure.

Thus, method 200 provides for determining fuel composition using an exhaust humidity sensor. The measured water content of the exhaust gas may also be used to control the operation of a heater configured to heat an exhaust gas sensor disposed in the exhaust passage of the engine. FIG. 3 illustrates a method 300 for controlling an exhaust gas sensor heater based on feedback from a humidity sensor. The exhaust gas sensor heater may be positioned near or in an exhaust gas sensor, and may be activated in order to heat the sensor when the sensor is below its operating temperature. The exhaust gas sensor may be an oxygen sensor used for air-fuel ratio feedback control, such as sensor 126. If condensate has settled on the sensor, when the heater is activated and the sensor rapidly increases in temperature, evaporation of the condensate may lead to cracking of the sensor. Thus, feedback from the humidity sensor may indicate if condensate has likely collected on the sensor, and if so, the heater may be controlled to prevent rapid evaporation of the condensate.

Method 300 includes, at 302, determining engine operating parameters. The engine operating parameters may include engine temperature, exhaust gas temperature, whether the engine is operating with cold start conditions, etc. At 304, it is determined if the exhaust gas sensor is below its operating temperature. The operating temperature may be the temperature at which the sensor starts to function efficiently, determined by the manufacturer of the exhaust gas sensor, and may be a fixed value such as 300° C. The sensor may be heated by the exhaust gas; however, the time lag associated with heating the sensor via the exhaust may result in unsatisfactory air-fuel ratio control, leading to increased emissions. To prevent this, a heating element in the sensor may be activated to rapidly heat the sensor when it is determined the sensor is below operating temperature. Determining the sensor is below operating temperature may include determining if the engine is operating with a cold engine start, estimating the sensor temperature based on engine temperature or exhaust gas temperature, or directly measuring sensor temperature.

If it is determined the sensor is not below operating temperature, method 300 proceeds to 306 to maintain current operating parameters, and then method 300 returns. If the sensor is below operating temperature, method 300 proceeds to 308 to determine the dew point of the exhaust based on the humidity sensor output. The dew point of the exhaust is the temperature below which the water vapor exhaust will condense into liquid water, and may be determined based on the relative humidity of the exhaust (determined by the humidity sensor) and the exhaust pressure. Determining the dew point may also include, at 310, adjusting the humidity sensor output based on the amount of water stored or released in a catalyst upstream of the humidity sensor. If a catalyst or other exhaust component is disposed in the exhaust passage between the exhaust gas sensor and the humidity sensor, the relative humidity determined by the humidity sensor may not reflect the relative humidity at the exhaust gas sensor due to water stored by or released from the catalyst. Additional information about determining the amount of stored or released water in the catalyst is presented below with respect to FIG. 4.

At 312, it is determined if the dew point is less than the exhaust gas sensor temperature. If the dew point is less than the exhaust gas sensor temperature, condensate will not form on the sensor, and thus method 300 proceeds to 316 to activate the heater. However, if the dew point is not less than the exhaust gas sensor temperature, condensate may form on the sensor. Thus, method 300 proceeds to 314 to deactivate the heater until the sensor temperature exceeds the dew point. The sensor may be slowly heated by the exhaust gas when the heater is deactivated. By waiting to activate the heater until the temperature of the sensor is greater than the dew point, rapid evaporation of the condensate on the sensor may be avoided. However, in some embodiments, rather than deactivating the heater, the heater may be adjusted to heat the sensor more slowly than if no condensate was present.

Whether the heater is activated immediately at 316 or whether the heater is deactivated until the exhaust gas sensor temperature is greater than the dew point at 314, method 300 proceeds to 318 to determine if the sensor is at operating temperature. If the sensor has not yet reached operating temperature, method 300 loops back to 316 to continue to activate the heater. If the sensor is at operating temperature, method 300 proceeds to 320 to deactivate the heater, and then method 300 returns.

Thus, the methods 200 and 300 of FIGS. 2 and 3 provide for various parameter adjustments based on feedback from a humidity sensor disposed in an exhaust passage of an engine. The humidity reading output from the humidity sensor may be affected by a catalyst upstream of the sensor, and thus the effect of the catalyst on the downstream water content may be determined to increase the accuracy of the humidity sensor readings. A catalyst water storage model may be used to predict when the catalyst is storing water, and how much water is stored in the catalyst. Further, the catalyst water storage model may predict when and how much water is released by the catalyst. By correcting the humidity sensor output based on the stored/released water, the readings of the humidity sensor used in the above methods may be of greater accuracy. Further, as explained in more detail with respect to FIG. 5, the catalyst water storage model along with current output from the humidity sensor may be used to diagnose degradation of the catalyst.

Figure 4:
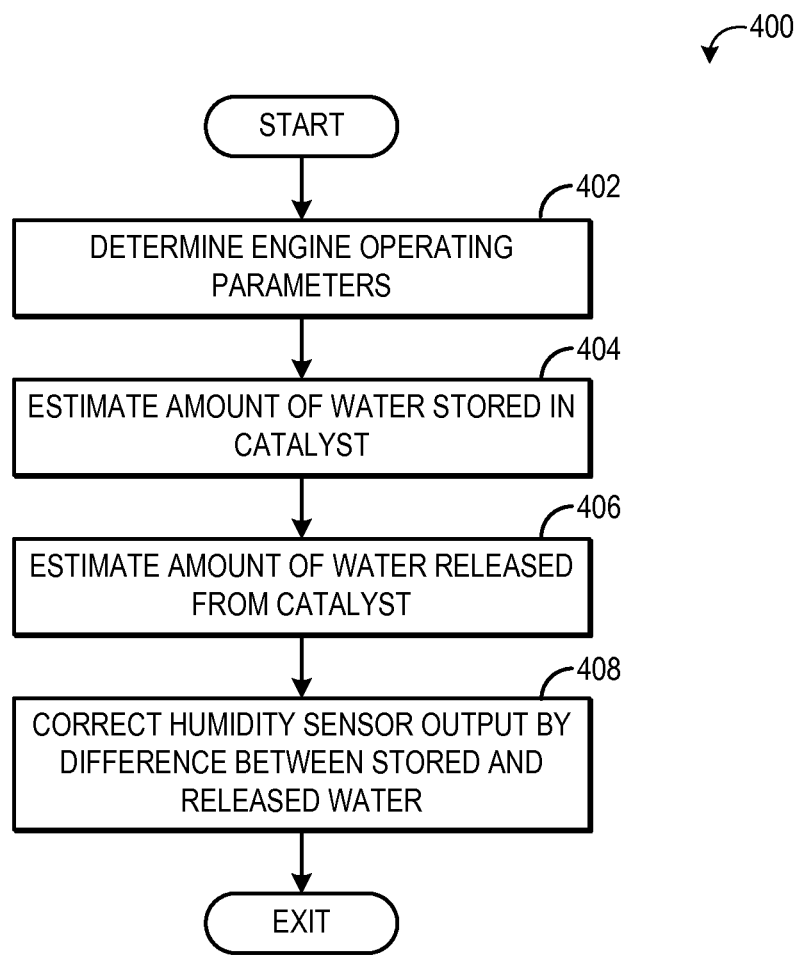
FIG. 4 is a flow chart illustrating a method for correcting humidity sensor output according to an embodiment of the present disclosure.

FIG. 4 illustrates a method 400 for correcting a humidity sensor using a catalyst water storage model. Method 400 may be carried out by controller 12 to correct output from sensor 128 arranged downstream of catalyst 70. Method 400 includes, at 402, determining engine operating parameters. The determined operating parameters may include engine speed, engine load, exhaust temperature, air-fuel ratio, elapsed time since an engine start, and/or other parameters. At 404, the amount of water stored in the catalyst is estimated. The amount of stored water may be estimated based on a plurality of parameters. For example, the water content of the exhaust upstream of the catalyst, pressure ratio across the catalyst, and catalyst temperature may be used to predict whether water is being stored in the catalyst. The water content of the exhaust upstream of the catalyst may be estimated based on the humidity of the intake air and water content produced during combustion. The humidity of the intake air may be determined using the exhaust humidity sensor during non-fueling conditions, or it may be determined from an intake humidity sensor. The water content produced during combustion may be based on air-fuel ratio, mass air flow, and fuel composition (determined using method 200 of FIG. 2 in one example). Additionally, if the engine includes an exhaust gas recirculation system that routes a portion of the exhaust gas back to the intake of the engine, the humidity of the exhaust gas and/or the amount of exhaust diverted away from the catalyst may also be used to determine the stored water content.

Thus, the water storage in the catalyst may be determined by estimating the water content of the exhaust, which is based on the water content of the intake air and the water produced during combustion. The amount of water that may accumulate in the catalyst may then be determined based on the estimated water content and the temperature of the catalyst (which may be directly measured or estimated based on exhaust gas temperature), and in some embodiments, also based on the pressure ratio across the catalyst. However, in other embodiments, the amount of stored catalyst water may be mapped to one or two simpler inputs, such as engine load and catalyst temperature.

At 406, the amount of water released from the catalyst is estimated. Depending on the temperature of the catalyst, the amount of released water may be a function of catalyst temperature, the amount of water previously stored in the catalyst (determined as described above), and the mass flow of the exhaust through the catalyst. For example, at catalyst temperatures below light-off, the water being released (e.g., evaporated) from the catalyst may be the water that has previously accumulated in the catalyst but is now evaporating as the catalyst heats. However, around the light-off temperature, constituents present in the exhaust gas (e.g., NOx, unburnt hydrocarbons, CO) may be reduced in the catalyst, releasing water as a byproduct of the reactions. Thus, determining the amount of released water may include determining both the amount of previously stored water currently being released and the amount of water produced by the catalyst reactions. Whether one or both of these water sources is being released is dependent on the temperature of the catalyst. For example, below the light-off temperature, nearly all the released water may be evaporated water that had previously accumulated in the catalyst. Then, by the time the catalyst reaches light-off temperature, all the accumulated water may have evaporated, and thus the released water may be water produced by the reactions occurring in the catalyst.

The amount of water released by the reduction reactions of the exhaust gas constituents may be determined based on air-fuel ratio, engine load, and engine temperature, as well as catalyst temperature. Additionally, if the amount of released water is being determined following an engine cold start, the amount of water released by the exhaust gas constituents may include reactions occurring with constituents that have been stored in the catalyst during cold catalyst operation (e.g., before light-off temperature was reached). Thus, the specifics of the catalyst (such as type of catalyst, size, etc.) as well as time since light-off temperature was reached may also be used to determine the amount of released water.

At 408, the humidity sensor output may be corrected based on the water storage and release of the catalyst. For example, the humidity sensor output may be corrected by the difference between the estimated stored and released water. Thus, if more water is being stored than released, the output of the humidity sensor may be adjusted to reflect a higher-than-measured exhaust gas water content. If more water is being released than stored, the output of the humidity sensor may be adjusted to reflect a lower-than-measured exhaust gas water content.

In this way, a catalyst water storage model may be used to estimate at which catalyst temperatures water will be stored and/or released from the catalyst in order to correct output from the humidity sensor downstream of the catalyst. However, the catalyst water storage model and output from the humidity sensor may also be used to diagnose degradation of the catalyst. Specifically, as the catalyst ages, it may take a longer amount of time to reach light-off temperature, and/or the light-off temperature of the catalyst may increase or otherwise change. The catalyst water storage model may be used to predict when water is being stored and when water is being released from the catalyst, and the output of the humidity sensor may be used to determine if the water is actually being stored and released as predicted. If a designated amount of water is predicted to be released from the catalyst at light-off temperature, but the humidity sensor indicates the water is actually being released at a temperature higher than the light-off temperature, for example, engine operating parameters may be adjusted to compensate for the delayed light-off time.

Figure 5:
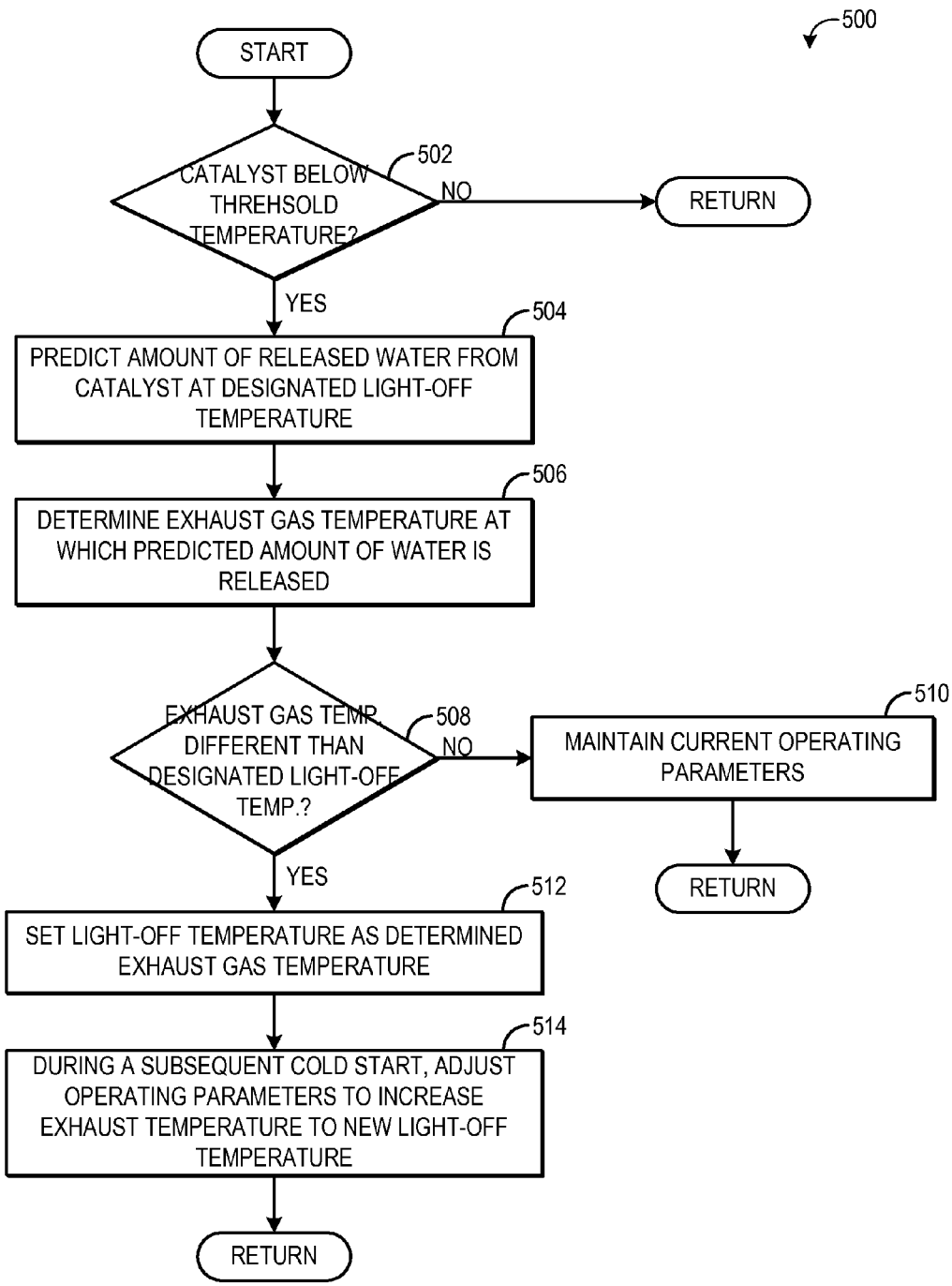
FIG. 5 is a flow chart illustrating a method for diagnosing a catalyst according to an embodiment of the present disclosure.

FIG. 5 illustrates a method 500 for diagnosing a catalyst using the catalyst water storage model and output from the humidity sensor. Method 500 may be carried out by the controller 12 during a suitable engine operating period, such as during and following an engine cold start, where the catalyst temperature increases to light-off temperature. Method 500 comprises, at 502, determining if the catalyst below a threshold temperature. The threshold temperature may be a designated catalyst light-off temperature (as determined from the catalyst manufacturer or from a previous diagnosis determination). If catalyst temperature is not below the threshold, method 500 returns. If the catalyst is below the threshold temperature, method 500 proceeds to 504 to predict the amount of released water from the catalyst at the designated light-off temperature. The amount of released water may be predicting using the catalyst water storage model, explained above with respect to FIG. 4, with an input of the designated light-off temperature as the catalyst temperature used to estimate the amount of released water. This amount of water is a prediction of the water the catalyst will release once it reaches light-off temperature. At 506, the exhaust gas temperature (or catalyst temperature) at which the predicted amount of water is released is determined. The amount of water actually released by the catalyst may be determined by the humidity sensor. As the humidity sensor outputs an indication of all the water content of the exhaust, the humidity due to intake air and combustion may be removed from the humidity sensor reading in one example.

At 508, it is determined if the exhaust gas temperature at which the predicted amount of water is actually released is different than the designated light-off temperature. The term "different than" may include any temperatures that are different than the light-off temperature. However, in other embodiments, the measured exhaust gas temperature may be different than the light-off temperature by more than a threshold amount, such as within 10° C. of the light-off temperature. Similarly, when determining at which temperature the actual amount of water released from the catalyst is equal to the predicted amount, equal to may include the exact same amounts, or it may include within a threshold range, such as within 5% of the predicted amount. If the exhaust gas temperature is not different than the designated light-off temperature, method 500 proceeds to 510 to maintain current operating parameters (as the determined light-off temperature is equal to the designated light-off temperature), and method 500 returns.

If the exhaust gas temperature is different than the designated light-off temperature, method 500 proceeds to 512 to set the actual light-off temperature of the catalyst as being equal to the measured exhaust gas temperature at which the predicted amount of water was released. At 514, engine operating parameters may be adjusted based on the newly-set light-off temperature. This may include, at a subsequent cold start, increasing the exhaust gas temperature to a higher temperature, increasing the exhaust temperature more quickly, etc., than when operating with the designated light-off temperature. Because the catalyst is operating with a different light-off temperature than previous operations, to prevent increased exhaust emissions, the catalyst is heated to the new light-off temperature by the exhaust gas. To increase the exhaust temperature more quickly or to a higher temperature, spark timing may be retarded, air-fuel ratio may be adjusted, an engine cooling circuit may be adjusted, etc. For example, the engine cooling circuit may include a valve controllable to adjust the amount of coolant cooled by an engine heat exchanger. To heat the exhaust, the amount of coolant that is cooled may be reduced, thus causing a rise in engine and exhaust temperatures. Other operating parameters may also be adjusted, such as the boost pressure of the engine (if the engine is turbocharged), amount of exhaust gas recirculation, etc. Further, if the light-off temperature of the catalyst has changed by a relatively large amount, an operator may be notified that the catalyst is degraded.

Thus, method 500 of FIG. 5 may diagnose a catalyst light-off temperature by comparing the humidity of the exhaust gas to an expected exhaust gas humidity at catalyst light-off temperature. If the humidities are not equal (or within a threshold range, such as 5%), it may be determined that the catalyst is not operating with the expected catalyst light-off temperature. To prevent increased emissions when the light-off temperature is different than expected, engine operating parameters may be adjusted. For example, spark timing may be retarded and/or air-fuel ratio increased to increase exhaust gas temperature to the new light-off temperature.

FIGS. 6 and 7 illustrate various engine operating parameters during execution of the above-described methods in a flex-fuel vehicle configured to operate with varying types of fuel. For example, the vehicle may operate with gasoline fuel and on a subsequent tank refill, may operate with E85 fuel. Specifically, diagram 600 of FIG. 6 illustrates exhaust temperature, fuel alcohol content, exhaust humidity, exhaust gas sensor heater operation, and catalyst water storage level during an engine cold start (e.g., when the engine is operating from ambient temperature at start-up) with gasoline fuel. Diagram 700 of FIG. 7 illustrates exhaust temperature, fuel alcohol content, exhaust humidity, exhaust gas sensor heater operation, and catalyst water storage level during an engine cold start with E85 fuel (85% ethanol, 15% gasoline). For each diagram, time is illustrated on the horizontal axis, while each respective operating parameter is illustrated on the vertical axis.

Referring first to FIG. 6, exhaust temperature during the cold start is illustrated by curve 602. At start-up, the engine may be operating with relatively low exhaust temperature, such as ambient temperature. As the engine warms up, exhaust temperature also increases. The engine is operating with gasoline fuel (or a fuel that otherwise is comprised of little to no alcohol). As shown by curve 604, the fuel alcohol content of the fuel injected to the engine is 0%.

Further, as depicted by curve 606, exhaust humidity (measured by humidity sensor 128) remains relatively constant during the initial stage of the cold start (before time $T_1$). Also during the beginning of the time depicted in diagram 600, the dew point is greater than the temperature of the exhaust gas sensor (which may be at a relatively similar temperature as the exhaust), and thus the exhaust gas sensor heater is off, as illustrated by curve 608. However, at time $T_1$, the temperature of the exhaust gas sensor increases above the dew point, and the heater is turned on.

The engine may also include a catalyst in the exhaust passage. When the catalyst is cold immediately following the engine start, it may store water (e.g., condensate may accumulate within the catalyst). Thus, as shown by curve 610, the amount of water stored in the catalyst may gradually increase as the humid exhaust travels through the catalyst. However, as the catalyst begins to warm due to the increasing temperature of the exhaust, the amount of condensate that accumulates in the catalyst may decrease. At time $T_3$, the exhaust temperature may be sufficiently high (and be flowing at a sufficiently high velocity) to heat the catalyst to a point where the stored water begins to be released (e.g., the condensate beings to evaporate). As a result, the amount of stored water in the catalyst begins to decrease until no water remains in the catalyst. The released water from the catalyst may be reflected in the exhaust humidity measured by the humidity sensor, which as shown in curve 606, increases after time $T_3$ as the catalyst water is released.

Further, because the catalyst is storing water during most of the duration of time depicted by diagram 600, the exhaust humidity determined by the humidity sensor may be inaccurate if the humidity sensor is disposed downstream of the catalyst. For example, the water stored in the catalyst is not reaching the humidity sensor, and thus the sensor may be outputting a lower humidity level than the actual humidity upstream of the catalyst. As explained earlier, if the amount of water stored in the catalyst is known (for example, if it is estimated using the catalyst water storage model), the exhaust humidity determined by the sensor may be corrected to account for the catalyst water storage.

Referring now to FIG. 7, exhaust gas temperature, illustrated by curve 702, starts low and rises as the engine warms up during the cold start. The engine is injecting E85 fuel, and as such the fuel alcohol content illustrated by curve 704 is at approximately 85%. Because E85 fuel produces more water during combustion than gasoline fuel, the exhaust humidity depicted in curve 706 is higher than the exhaust humidity depicted by curve 606 of FIG. 6. Due to the higher amount of exhaust humidity, the dew point of the exhaust may be higher, and as such the exhaust temperature may increase to a higher temperature before the heater is turned on than when the engine operates with gasoline fuel. Thus, the exhaust gas sensor heater, illustrated by curve 708, is turned on at time $T_2$, which is delayed compared to when the exhaust gas sensor heater was activated in diagram 600. Additionally, the amount of water stored in the catalyst is greater when operating with E85 fuel than with gasoline fuel, which is illustrated in curve 710. However, similar to the water storage illustrated in FIG. 6, once the exhaust temperature reaches a high enough temperature, the water in the catalyst is released after time $T_3$, and the exhaust humidity increases.

It will be appreciated that the configurations and methods disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an engine, comprising:
    based on a dew point of exhaust gas, adjusting an exhaust gas sensor heater configured to heat an exhaust gas sensor disposed in an exhaust passage of the engine, the dew point based on output from a humidity sensor disposed in the exhaust passage, and
    adjusting a fuel injection amount based on output from the humidity sensor,
    wherein the dew point is determined based on relative humidity of the exhaust gas determined by the humidity sensor, exhaust gas temperature, and exhaust gas pressure.

2. The method of claim 1, wherein adjusting the exhaust gas sensor heater further comprises deactivating the exhaust gas sensor heater if the dew point is greater than a temperature of the exhaust gas sensor.

3. The method of claim 1, wherein adjusting the exhaust gas sensor heater further comprises activating the exhaust gas sensor heater if the dew point is less than a temperature of the exhaust gas sensor and exhaust gas temperature is below a threshold.

4. The method of claim 1, further comprising adjusting exhaust gas temperature based on output from the humidity sensor.

5. A method for an engine, comprising:
    determining a light-off temperature of a catalyst disposed in an exhaust passage of the engine based on exhaust gas water content measured by a humidity sensor disposed in the exhaust passage downstream of the catalyst; and
    during engine cold start conditions,
        predicting an amount of water to be released from the catalyst when the catalyst reaches light-off temperature;
        setting the light-off temperature as an exhaust gas temperature at which the predicted amount of water is released from the catalyst; and
        adjusting engine operating parameters to increase exhaust gas temperature above the light-off temperature.

6. The method of claim 5, further comprising determining that the predicted amount of water has been released from the catalyst based on output from the humidity sensor.

7. The method of claim 5, wherein the predicted amount of water to be released from the catalyst is estimated based on an amount of exhaust gas constituents stored in the catalyst during cold start conditions.

8. The method of claim 5, wherein adjusting engine operating parameters to increase exhaust gas temperature further comprises adjusting air-fuel ratio.

9. The method of claim 5, wherein adjusting engine operating parameters to increase exhaust gas temperature further comprises retarding spark timing.

10. A method performed by an electronic controller in combination with an engine and one or more sensors, comprising:
adjusting via the electronic controller a measured exhaust gas water content based on water storage and release in a catalyst, the exhaust gas water content measured by a humidity sensor disposed in an exhaust passage of the engine; and
adjusting a fuel injection amount injected by an injector based on the adjusted exhaust gas water content.

11. The method of claim 10, wherein the catalyst is positioned upstream of the humidity sensor, and wherein the water storage and release is determined based on an amount of water produced during combustion and catalyst temperature.

12. The method of claim 11, wherein the amount of water produced during combustion is estimated based on intake air humidity, air-fuel ratio, and fuel composition.

13. The method of claim 12, wherein the fuel composition is determined based on output from the humidity sensor.

14. The method of claim 10, wherein adjusting the measured exhaust gas water content further comprises, if water is being released from the catalyst, decreasing the measured exhaust gas water content by an amount of released water.

15. The method of claim 10, wherein adjusting the measured exhaust gas water content further comprises, if water is being stored in the catalyst, increasing the measured exhaust gas water content by an amount of stored water.

16. The method of claim 10, wherein adjusting the fuel injection amount further comprises increasing the fuel injection amount if the adjusted exhaust gas water content is greater than a threshold, and decreasing the fuel injection amount if the adjusted exhaust gas water content is less than the threshold.

17. The method of claim 12, wherein the humidity sensor is a first humidity sensor, and further comprising determining the intake air humidity based on output from a second humidity sensor disposed in an intake passage of the engine.

18. The method of claim 10, further comprising determining a dew point of exhaust gas based on the adjusted exhaust gas water content and adjusting an exhaust gas sensor heater configured to heat an exhaust gas sensor disposed in the exhaust passage of the engine based on the dew point of the exhaust gas.

19. The method of claim 18, wherein adjusting the exhaust gas sensor heater further comprises deactivating the exhaust gas sensor heater if the dew point is greater than a temperature of the exhaust gas sensor.

20. The method of claim 18, wherein adjusting the exhaust gas sensor heater further comprises activating the exhaust gas sensor heater if the dew point is less than a temperature of the exhaust gas sensor and exhaust gas temperature is below a threshold.

21. The method of claim 10, comprising:
determining a light-off temperature of the catalyst based on exhaust gas water content measured by the humidity sensor; and
during cold start conditions, adjusting engine operating parameters to increase exhaust gas temperature above the light-off temperature.

22. The method of claim 21, wherein determining the light-off temperature further comprises:
during engine cold start conditions, predicting an amount of water to be released from the catalyst when the catalyst reaches light-off temperature; and
setting the light-off temperature as an exhaust gas temperature at which the predicted amount of water is released from the catalyst.

23. The method of claim 22, further comprising determining that the predicted amount of water has been released from the catalyst based on output from the humidity sensor.

24. The method of claim 23, wherein the predicted amount of water to be released from the catalyst is estimated based on an amount of exhaust gas constituents stored in the catalyst during cold start conditions.

25. The method of claim 10, further comprising determining an amount of water stored in the catalyst based on engine load and catalyst temperature, and determining an amount of water released from the catalyst based on catalyst temperature, an amount of water previously stored in the catalyst, and mass flow of exhaust through the catalyst.

26. The method of claim 10, further comprising adjusting spark timing of a spark plug based on the adjusted exhaust gas water content.

* * * * *